(12) United States Patent
Matulis et al.

(10) Patent No.: US 8,314,132 B2
(45) Date of Patent: Nov. 20, 2012

(54) 5-ARYL-4-(5-SUBSTITUTED 2,4-DIHYDROXYPHENYL)-1,2,3-THIADIAZOLES AS INHIBITORS OF HSP90 CHAPERONE AND THE INTERMEDIATES FOR PRODUCTION THEREOF

(75) Inventors: Daumantas Matulis, Vilnius (LT); Inga Cikotiene, Vilnius (LT); Egidijus Kazlauskas, Vilnius (LT); Jurgita Matuliene, Vilnius (LT)

(73) Assignee: Biotechnologijos Institutas (LT)

( * ) Notice: Subject to any disclaimer, the term of this patent is extended or adjusted under 35 U.S.C. 154(b) by 0 days.

(21) Appl. No.: 12/990,551

(22) PCT Filed: Jun. 18, 2008

(86) PCT No.: PCT/LT2008/000003
§ 371 (c)(1),
(2), (4) Date: Nov. 1, 2010

(87) PCT Pub. No.: WO2009/134110
PCT Pub. Date: Nov. 5, 2009

(65) Prior Publication Data
US 2011/0046387 A1 Feb. 24, 2011

(30) Foreign Application Priority Data
Apr. 30, 2008 (LT) .................................... 2008 035

(51) Int. Cl.
*A61K 31/433* (2006.01)
*C07D 285/06* (2006.01)
*C07C 243/18* (2006.01)

(52) U.S. Cl. .......................... 514/361; 548/127; 564/251
(58) Field of Classification Search .................. 514/361; 548/127; 564/251
See application file for complete search history.

(56) References Cited

FOREIGN PATENT DOCUMENTS
CN 1865252 A * 11/2006
* cited by examiner

Primary Examiner — Yong Chu
(74) Attorney, Agent, or Firm — Berliner & Associates

(57) ABSTRACT

Invention is related to novel compounds -5-aryl-4-(5-substituted 2,4-dihydroxyphenyl)-1,2,3-thiadiazoles with general formula (I). The compounds can be used in biomedicine as active ingredients in pharmaceutical formulations, because they inhibit Hsp90 chaperone which participate in cancer progression. This invention is also related to new intermediate compounds which are used for the synthesis of thiadiazoles of general formula (I).

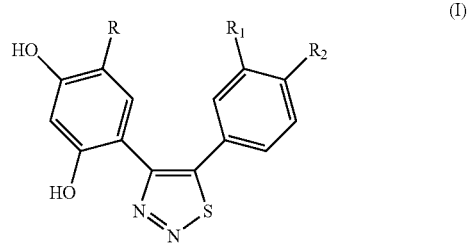

8 Claims, 3 Drawing Sheets

US 8,314,132 B2

5-ARYL-4-(5-SUBSTITUTED 2,4-DIHYDROXYPHENYL)-1,2,3-THIADIAZOLES AS INHIBITORS OF HSP90 CHAPERONE AND THE INTERMEDIATES FOR PRODUCTION THEREOF

FIELD OF THE INVENTION

The present invention describes novel 5-aryl-4-(5-substituted 2,4-dihydroxyphenyl)-1,2,3-thiadiazole derivatives, potentially useful in biomedicine as active ingredients of pharmaceutical preparations due to their ability to inhibit Hsp90 chaperone participating in cancer-disease progression. The invention also relates to new intermediate compounds required for the synthesis of target thiadiazoles.

BACKGROUND OF THE INVENTION

Molecular chaperones are protein machines that are responsible for the correct folding, stabilization, and function of other proteins in the cell. Exposure of cells to environmental stress, including heat shock, alcohols, heavy metals or oxidative stress, results in the cellular accumulation of these chaperones, commonly known as heat shock proteins (Hsp's). Heat-shock protein 90 (Hsp90) constitutes about 1-2% of total cellular proteins and is usually present in the cell as a dimer. It is a molecular chaperone responsible for ATP-depended folding, stability and function of many "client" proteins that are involved in the development and progression of cancer. These client proteins include ErbB2, c-Raf, Cdk4, mutant p53, hTERT, Hifl-$\alpha$, and the estrogen/androgen receptors. Inhibition of Hsp90 causes the simultaneous, combinatorial destabilization and degradation of the oncogenic client proteins, leading in turn to a multiprolonged attack on all of the hallmark traits of cancer, including unrestricted proliferation and survival, invasion, metastasis and angiogenesis. It is generally thought that cancer cells are more susceptible to Hsp90 inhibition than are the corresponding normal cells (P. Workman (2004), *Trends Mol. Med.*, 10, 47-51). On the other hand, therapeutic selectivity of Hsp90 inhibitors is the stressed condition of cancer cells, due both to oncogenic mutations and deregulated signalling and also to environmental factors such as hypoxia, acidosis and nutrient deprivation. Moreover, it has been reported that the Hsp90 found in malignant cells exists predominantly in a superchaperone complex that binds Hsp90 inhibitors much more effectively than the uncomplexed form that is mainly present in healthy cells (B. W. Dymock et al, (2004), *Expert Opin. Ther. Patents*, 14, 837-847).

The ATPase activity of Hsp90 chaperone can be inhibited with some selectivity by natural product antibiotics such as geldanamycin and radicicol (S. M. Roe et al, (1999), *J Med Chem* 42, 260-266). Both of those compounds bind to the N-terminal domain of Hsp90 and inhibit the intrinsic ATPase activity.

Geldanamycin showed activity in human tumour xenograft models but this compound proved to be too hepatotoxic for clinical development. However, the modified versions of geldanamycin—17-allylamino-17-demethoxy-geldanamycin (17-AAG) and 17-dimethylaminoethylamino-17-demethoxygeldanamycin (17-DMAG) retain the property of Hsp90 inhibition and have significantly less hepatotoxicity than geldanamycin (U.S. Pat. No. 4,261,989, publ. 1981). 17-AAG is currently being evaluated in clinical trials.

Radicicol is macrocyclic antibiotic isolated from *Monosporium Bonorden*. Radicicol is more potent inhibitor of Hsp90 ATPase activity than geldanamycin or 17-AAG (T. W. Schulte et al, (1998) *Cell Stress Chaperones* 3, 100-108). Unfortunately, the radicicol structure has some inherent limitations, including the epoxide moiety, keto group ant the propensity to undergo Michael addition reactions. Radicicol lacks antitumour activity in vivo due to the unstable chemical nature of the compound. Oxime derivatives of radicicol (known as KF25706 and KF58333) have been synthesized and retain the Hsp90 inhibitory activity of radicicol. Moreover KF25706 has been shown to exhibit in vivo antitumour activity in human tumour xenograft models (S. Soga et al (1999) *Cancer Res*, 59, 2931-8; U.S. Pat. No. 6,239,168; U.S. Pat. No. 6,316,491; U.S. Pat. No. 6,635,662). However, no radicicol derivative has progressed to clinical development.

It is also known that coumarin, novobiocin, and cisplatin bind to the C-terminal domain of Hsp90 resulting in the inhibition of ATPase function (G. A. Holdgate (1997) *Biochemistry* 36, 9663-9673; R. J. Lewis (1996) *Embo J* 15, 1412-1420; M. G. Marcu et al (2000) *J. Biol. Chem.*, 275, 37181-37186; M. G. Marcu et al (2003) *Curr. Cancer Drug Targets*, 3, 343). Therefore, both binding sites of Hsp90 are important to Hsp90 chaperone properties.

Significant consideration in the patent literature is given to various synthetic small molecule Hsp90 inhibitors. First purine-based inhibitors (PU3 and PU24FCl) have been synthesized based on rational drug design with the aid of the X-ray crystal structure (EP 1335920, G. Chiosis et al (2001) *Chem. Biol.* 8, 289-299). These agents were shown to result in the degradation of signaling molecules, including ERBB2, and to cause cell cycle arrest and differentiation in breast cancer cells. Recently, S. R. Kasibhatla et al have reported about novel purine derivatives with amine, sulfide, sulfoxide and sulfone moieties (WO 03037860; U.S. Pat. No. 7,241, 890; U.S. Pat. No. 7,138,401). Some of these compounds inhibit Hsp90 chaperone in nanomolar potency. Nowadays purine-based inhibitors of Hsp90 attract scientific attention (WO2006075095, EP1838322).

Another class of synthetic Hsp90 inhibitors are presented by structural purine analogs—pyrazolopyrimidines, pyrrolopyrimidines and triazolopyrimidines. These compounds were synthesized and tested by S. R. Kasibhatla et al (U.S. Pat. No. 7,148,228; U.S. Pat. No. 7,138,402, U.S. Pat. No. 7,129,244, EP1869027).

Various 3,4-diarylpyrazole derivatives bearing resorcinol moiety have been selected and prepared by high throughput screening of a combinatorial library at the Institute of Cancer Research. Some of such derivatives (known as CCT 018159, VER 49009) showed very high Hsp90 inhibition affinity (K. M. J. Cheung et al (2005) *Bioorg. Med. Chem. Lett.*, 15, 3338-3343; B. W. Dymock et al (2005) *J. Med. Chem.*, 48, 4212-4215; U.S. Pat. No. 7,247,734; EP 1456180). A number of 3-arylpyrazole-4-piperazine derivatives (X. Barril (2006) *Bioorg. Med. Chem. Lett.*, 16, 2543-2548), as well as 3-aryl-4-aryloxypyrazoles (patent JP 2005225787) are synthesized and exhibited Hsp90 binding affinity.

It is also patented that pyrazole scaffold in 3,4-diarylpyrazoles can be replaced by other 5-membered ring, such as isoxazole (EP1611112) or triazole (WO2005000300, WO2007139952).

Also a large number of small-molecule synthetic inhibitors of Hsp90 chaperone have been synthesized and evaluated. This is different pyrazole (US2007112192, EP1567151, US2007191445, EP1620090, JP2006306755), triazole (US2007155809, WO2007139956, WO2008021364, WO2006055760, WO2007139968, WO2007139967, WO2007139952, US2006167070), quinazolines (EP1885701, WO2006122631), isoindoles (WO2008044034, EP 1869042) and hydroxybenzamides (WO2006109075).

Despite the fact that a large number of different Hsp90 inhibitors have been synthesized to date, only few of them are clinically tested. There still remains a great need of new potent Hsp90 inhibitors which offer one or more following advantages: improved activity, selectivity, solubility, reduced toxicity and side-effects, reduced cost of synthesis and so on.

Therefore, the creation of novel Hsp90 chaperone inhibitors is still an important task.

No data on synthesis of invention compounds 5-aryl-4-(5-substituted 2,4-dihydroxyphenyl)-1,2,3 thiadiazoles and intermediate compounds required for the synthesis of invention compounds was found in patent and non-patent literature.

SUMMARY OF THE INVENTION

This invention describes new 5-aryl-4-(5-substituted 2,4-dihydroxyphenyl)-1,2,3-thiadiazoles with general formula (I

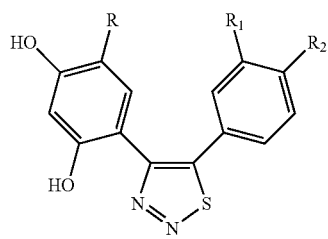

(I)

wherein

R is H, Cl, Br, I, $CH_3$, $C_2H_5$, $OCH_3$;

$R_1$ and $R_2$ are the same or different substituents, selected from the group, consisting of H, $CH_3$, $C_2H_5$, $C_3H_7$, $C_4H_9$, $OCH_3$, $OC_2H_5$, $OC_3H_7$, $O(CH_2)_2O$, $O(CH_2)_3O$.

The objects of the invention are also the non-toxic, pharmaceutically acceptable salts of the thiadiazoles of the general formula (I). They include all salts which retain activity comparable to original compounds and do not attain any harmful and undesirable effects. Such salts are obtained from compounds with general structural formula (I) by mixing their solution with pharmacologically acceptable non-toxic organic and inorganic acids, such as hydrogen chloride, butane diacid, citric acid, tartaric acid, phosphoric acid, sulphuric acid and other.

Examples of the invented compounds are compounds, selected from the group comprising:

4-[6-(4-chloro-1,3-dihydroxyphenyl)]-5-[4-(4-methoxyphenyl)]-1,2,3-thiadiazole;

4-[6-(4-chloro-1,3-dihydroxyphenyl)]-5-[4-(4-ethoxyphenyl)]-1,2,3-thiadiazole;

4-[6-(4-chloro-1,3-dihydroxyphenyl)]-5-[4-(4-methylphenyl)]-1,2,3-thiadiazole;

4-[6-(4-chloro-1,3-dihydroxyphenyl)]-5-[4-(3,4-dimethoxyphenyl)]-1,2,3-thiadiazole;

4-[6-(4-ethyl-1,3-dihydroxyphenyl)]-5-[4-(4-ethoxyphenyl)]-1,2,3-thiadiazole;

where all above listed compounds exhibit Hsp90 inhibitor properties.

The new intermediate compounds described below which could be used for the synthesis of thiadiazoles with general formula (I) are also subject of this invention.

DETAILED DESCRIPTION OF THE INVENTION

New compounds of the invention can be obtained according to general synthesis scheme:

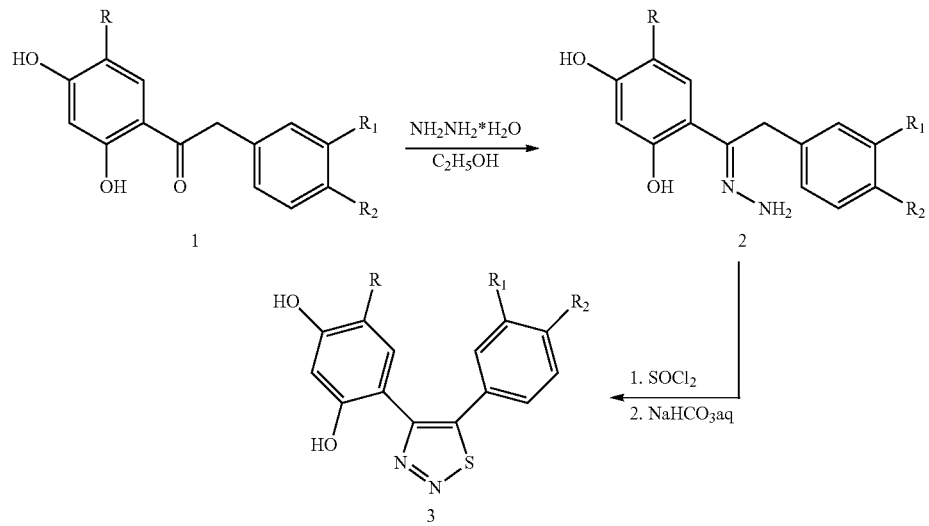

Synthesis of the starting materials (compounds with general formula 1) was accomplished by procedure described by B. W. Dymock, X. Barril, P. A. Brough, J. E. Cansfield, A. Massey, E. McDonald, R. E. Hubbard, A. Surgenor, S. D. Roughley, P. Webb, P. Workman, L. Wright, M. J. Drysdale (2005) *J. Med. Chem.*, 48, 4212-4215. Compounds 1 reacted with hydrazine hydrate in boiling ethanol and formed the corresponding hydrazones 2. Latter derivatives underwent smoothly cyclization with thionyl chloride to form 5-aryl-4-(5-substituted 2,4-dihydroxyphenyl)-1,2,3-thiadiazoles 3 in high yields.

BRIEF DESCRIPTION OF THE DRAWINGS

To illustrate the main characteristics of the new compounds this description contains.

EMBODIMENTS OF THE INVENTION

Figure 1:
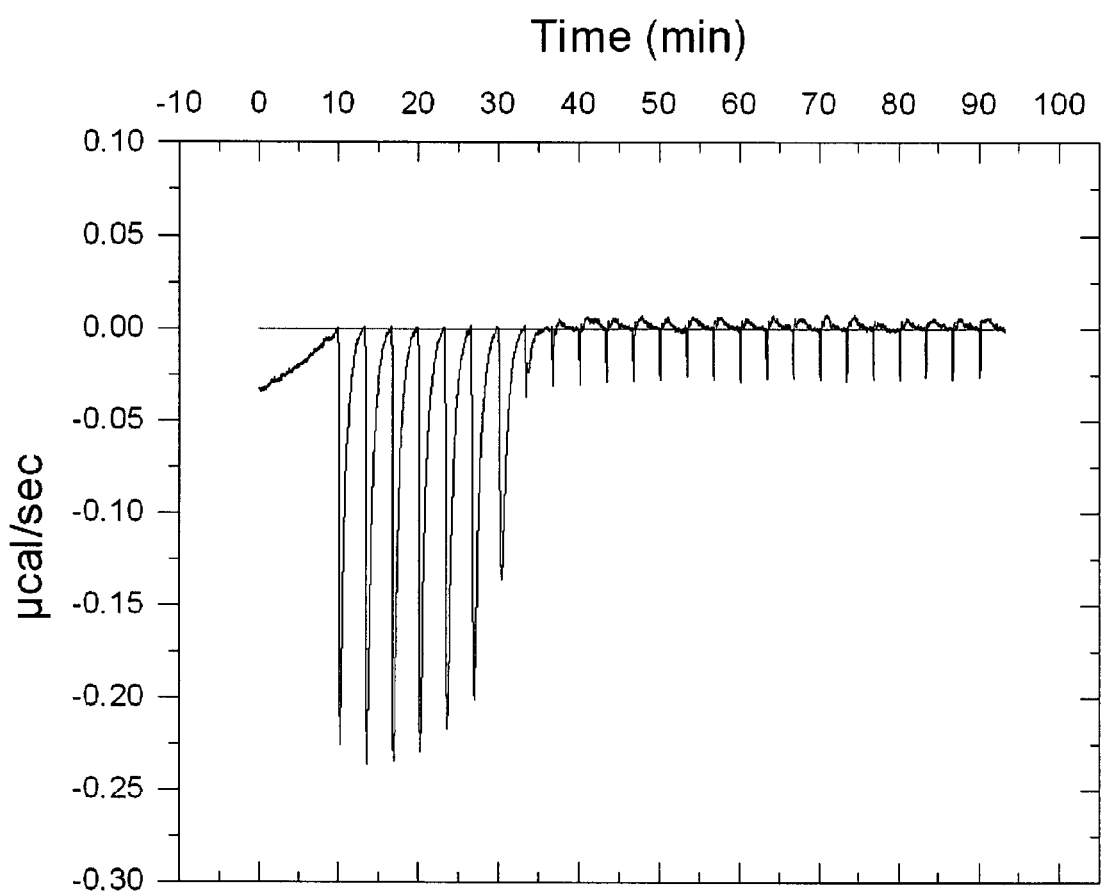
FIG. 1. Determination of the compound of general formula I, namely 4-(5-chloro-2,4-dihydroxyphenyl)-5-(4-ethoxyphenyl)-1,2,3-thiadiazole (3b) binding to Hsp90N by isothermal titration calorimetry. Raw isothermal titration calorimetric data is shown.

Represented below are specific examples of invention compounds and synthesis thereof, including intermediate compounds required for target compound. These examples are presented only for illustrative purpose of the invention; they do not limit the scope of the invention.

Example 1

Production of the Intermediate Compound 1-(5-chloro-2,4-dihydroxyphenyl)-2-(4-methoxyphenyl) ethanone hydrazone (2a)

Hydrazine hydrate (0.166 ml, 3.42 mmol) is added to a solution of 1-(5-chloro-2,4-dihydroxyphenyl)-2-(4-methoxyphenyl)ethanone (1a) (0.5 g, 1.71 mmol) in 95% ethanol (5 ml). The mixture is heated under reflux for 7 hours. Solvent is concentrated in vacuo, the residue treated with water, filtered of and recrystallyzed from 2-propanol.

Yield 76%, yellow solid, mp 143-145° C.
$^1$H NMR (300 MHz, DMSO-$d_6$) δ ppm 3.72 (3H, s, OCH$_3$), 4.00 (2H, s, CH$_2$), 6.40 (1H, s, ArH), 6.71 (2H, br.س. NH$_2$), 6.88 (2H, d, J=8.7 Hz, ArH), 7.15 (2H, d, J=8.7 Hz, ArH), 7.26 (1H, s, ArH), 9.92 (1H, br.s. OH), 13.56 (1H, s, OH).
$^{13}$C NMR (75 MHz, DMSO-$d_6$) δ ppm 28.6, 54.9, 104.1, 109.2, 113.0, 114.0, 127.2, 128.0, 129.1, 149.3, 153.2, 157.7, 158.4.

Example 2

Production of the Intermediate Compound 1-(5-chloro-2,4-dihydroxyphenyl)-2-(4-ethoxyphenyl) ethanone hydrazone (2b)

Synthesis was carried out according to the description of Example 1, starting from 1-(5-chloro-2,4-dihydroxyphenyl)-2-(4-ethoxyphenyl)ethanone 1b (0.52 g, 1.71 mmol).

Yield 97%, yellow solid, mp 163-165° C.
$^1$H NMR (300 MHz, DMSO-$d_6$) δ ppm 1.28 (3H, t, J=6.6 Hz, CH$_3$), 3.94 (2H, q, J=6.6 Hz, OCH$_2$), 3.94 (2H, s, CH$_2$), 6.39 (1H, s, ArH), 6.70 (2H, br.s. NH$_2$), 6.84 (2H, d, J=8.7 Hz, ArH), 7.11 (2H, d, J=8.7 Hz, ArH), 7.24 (1H, s, ArH), 10.18 (1H, br.s. OH), 13.55 (1H, s, OH).

Example 3

Production of the Intermediate Compound 1-(5-chloro-2,4-dihydroxyphenyl)-2-(4-methylphenyl) ethanone hydrazone (2c)

Synthesis was carried out according to the description of Example 1, starting from 1-(5-chloro-2,4-dihydroxyphenyl)-2-(4-methylphenyl)ethanone 1c (0.47 g, 1.71 mmol).

Yield 74%, yellow solid, mp 182-184° C.
$^1$H NMR (300 MHz, DMSO-$d_6$) δ ppm 3.33 (3H, s, CH$_3$), 3.79 (2H, s, CH$_2$), 6.41 (1H, s, ArH), 6.75 (2H, br.s. NH$_2$), 7.08-7.17 (4H, m, ArH), 7.28 (1H, s, ArH), 9.99 (1H, br.s. OH), 13.50 (1H, s, OH).

Example 4

Production of the Intermediate Compound 1-(5-chloro-2,4-dihydroxyphenyl)-2-(3,4-dimethoxyphenyl)ethanone hydrazone (2d)

Synthesis was carried out according to the description of Example 1, starting from 1-(5-chloro-2,4-dihydroxyphenyl)-2-(3,4-dimethoxyphenyl)ethanone 1d (0.55 g, 1.71 mmol).

Yield 83%, yellow solid, mp 152-154° C.
$^1$H NMR (300 MHz, DMSO-$d_6$) δ ppm 3.71 (3H, s, OCH$_3$), 3.73 (3H, s, OCH$_3$), 3.99 (2H, s, CH$_2$), 6.40 (1H, s, ArH), 6.65 (2H, br.s. NH$_2$), 6.68-6.94 (3H, m, ArH), 7.28 (1H, s, ArH), 10.02 (1H, br.s. OH), 13.52 (1H, s, OH).

Example 5

Production of the Intermediate Compound 1-(5-ethyl-2,4-dihydroxyphenyl)-2-(4-ethoxyphenyl)ethanone hydrazone (2e)

Synthesis was carried out according to the description of Example 1, starting from 1-(5-ethyl-2,4-dihydroxyphenyl)-2-(4-ethoxyphenyl)ethanone 1e (0.51 g, 1.71 mmol).

Yield 60%, yellow solid, mp 63-64° C.
$^1$H NMR (300 MHz, DMSO-$d_6$) δ ppm 1.17 (3H, t, J=7 Hz, CH$_3$), 1.39 (3H, t, J=7.5 Hz, CH$_3$), 2.42 (2H, q, J=7 Hz, CH$_2$), 3.72 (2H, q, J=7.5 Hz, OCH$_2$), 3.99 (2H, s, CH$_2$), 6.32 (1H, s, ArH), 6.54 (2H, br.s. NH$_2$), 6.75 (2H, d, J=8.7 Hz, ArH), 7.07 (2H, d, J=8.7 Hz, ArH), 7.21 (1H, s, ArH), 9.90 (1H, br.s. OH), 13.50 (1H, s, OH).

Example 6

Preparation of 4-(5-chloro-2,4-dihydroxyphenyl)-5-(4-methoxyphenyl)-1,2,3-thiadiazole (3a)

1-(5-chloro-2,4-dihydroxyphenyl)-2-(4-methoxyphenyl) ethanone hydrazone (2a) (0.1 g, 0.33 mmol) is carefully added to thionyl chloride (1 ml). The reaction mixture is stirred at room temperature for 2 hours. The excess of thionyl chloride is evaporated under reduced pressure, the residue is dissolved in chloroform (10 ml). The organic layer is washed twice with NaHCO$_3$ (sat. aq. 10 ml), then with water (15 ml), dried over Na$_2$SO$_4$, concentrated in vacuo. The residue was purified by dry column chromatography (D. S. Pederson, C. Rosenbohm, (2001) *Synthesis*, 16, 2431-2434).

Yield 95%, brown amorphous solid, mp 87-89° C.

$^1$H NMR (300 MHz, CDCl$_3$) δ ppm 3.93 (3H, s, OCH$_3$), 5.76 (1H, br.s. OH), 6.81 (1H, s, ArH), 7.05 (2H, d, J=8.7 Hz, ArH), 7.17 (1H, s, ArH), 7.39 (2H, d, J=8.7 Hz, ArH), 10.20 (1H, s, OH).

$^{13}$C NMR (75 MHz, DMSO-d$_6$) δ ppm 55.2, 103.9, 109.9, 110.3, 114.5, 120.1, 129.6, 131.4, 151.9, 153.4, 154.6, 155.2, 160.2

Example 7

Preparation of 4-(5-chloro-2,4-dihydroxyphenyl)-5-(4-ethoxyphenyl)-1,2,3-thiadiazole (3b)

Synthesis was carried out according to the description of Example 6, starting from 1-(5-chloro-2,4-dihydroxyphenyl)-2-(4-ethoxyphenyl)ethanone hydrazone 2b (0.11 g, 0.33 mmol).

Yield 80%, brownish amorphous solid, mp 132-134° C.

$^1$H NMR (300 MHz, DMSO-d$_6$) δ ppm 1.30 (3H, t, J=6.9 Hz, CH$_3$), 4.01 (2H, q, J=6.9 Hz, OCH$_2$), 5.92 (1H, br.s. OH), 6.71 (1H, s, ArH), 6.93 (2H, d, J=9 Hz, ArH), 7.24 (1H, s, ArH), 7.29 (2H, d, J=9 Hz, ArH), 10.23 (1H, s, OH).

$^{13}$C NMR (75 MHz, DMSO-d$_6$) δ ppm 15.2, 53.9, 104.7, 110.7, 111.1, 115.6, 120.8, 130.4, 132.2, 152.8, 154.2, 155.4, 156.0, 160.3.

Example 8

Preparation of 4-(5-chloro-2,4-dihydroxyphenyl)-5-(4-methylphenyl)-1,2,3-thiadiazole (3c)

Synthesis was carried out according to the description of Example 6, starting from 1-(5-chloro-2,4-dihydroxyphenyl)-2-(4-methylphenyl)ethanone hydrazone 2c (0.10 g, 0.33 mmol).

Yield 94%, brown amorphous solid, mp 69-71° C.

$^1$H NMR (300 MHz, DMSO-d$_6$) δ ppm 2.31 (3H, s, CH$_3$), 5.57 (1H, br.s. OH), 6.70 (1H, s, ArH), 7.20-7.27 (4H, m, ArH), 7.29 (1H, s, ArH), 10.22 (1H, s, OH).

$^{13}$C NMR (75 MHz, DMSO-d$_6$) δ ppm 21.5, 104.7, 110.7, 111.0, 126.0, 128.8, 130.3, 132.3, 140.2, 152.9, 154.7, 155.4, 156.0.

Example 9

Preparation of 4-(5-chloro-2,4-dihydroxyphenyl)-5-(3,4-dimethoxyphenyl)-1,2,3-thiadiazole (3d)

Synthesis was carried out according to the description of Example 6, starting from 1-(5-chloro-2,4-dihydroxyphenyl)-2-(3,4-dimethoxyphenyl)ethanone hydrazone 2d (0.11 g, 0.33 mmol).

Yield 96%, brownish amorphous solid, mp 117-119° C.

$^1$H NMR (300 MHz, DMSO-d$_6$) δ ppm 3.60 (3H, s, OCH$_3$), 3.77 (3H, s, OCH$_3$), 5.78 (1H, br.s. OH), 6.73 (1H, s, ArH), 6.94-6.98 (3H, m, ArH), 7.26 (1H, s, ArH), 10.21 (1H, s, OH).

$^{13}$C NMR (75 MHz, DMSO-d$_6$) δ ppm 55.2, 55.5, 103.9, 109.9, 110.5, 111.4, 111.9, 120.2, 121.6, 131.6, 148.5, 149.9, 152.2, 153.6, 154.7, 155.5.

Example 10

Preparation of 4-(5-ethyl-2,4-dihydroxyphenyl)-5-(4-ethoxyphenyl)-1,2,3-thiadiazole (3e)

Synthesis was carried out according to the description of Example 6, starting from 1-(5-ethyl-2,4-dihydroxyphenyl)-2-(4-ethoxyphenyl)ethanone hydrazone 2e (0.10 g, 0.33 mmol).

Yield 65%, brown amorphous solid, mp 65-66° C.

$^1$H NMR (300 MHz, DMSO-d$_6$) δ ppm 1.08 (3H, t, J=6.6 Hz, CH$_3$), 1.319 (3H, t, J=7 Hz, CH$_3$), 2.44 (2H, q, J=6.6 Hz, CH$_2$), 4.03 (2H, q, J=7.5 Hz, OCH$_2$), 5.87 (1H, br.s. OH), 6.47 (1H, s, ArH), 6.94 (2H, d, J=7.5 Hz, ArH), 7.99 (1H, s, ArH), 7.31 (2H, d, J=7.5 Hz, ArH), 10.02 (1H, s, OH).

Compounds of general formula (I) bearing different substituents in aromatic rings (R=Br, I, OCH$_3$; R$_1$, R$_2$=OC$_3$H$_7$, C$_2$H$_5$, C$_3$H$_7$, C$_4$H$_9$, O(CH$_2$)$_2$O, O(CH$_2$)$_3$O and others) can be synthesized in a similar way to compounds 3a-e starting from corresponding 1-(5-substituted-2,4-dihydroxyphenyl)-2-(3,4-disubstitutedphenyl)ethanones.

Example 11

Determination of Binding Constants by Isothermal Titration Calorimetry

Figure 2:
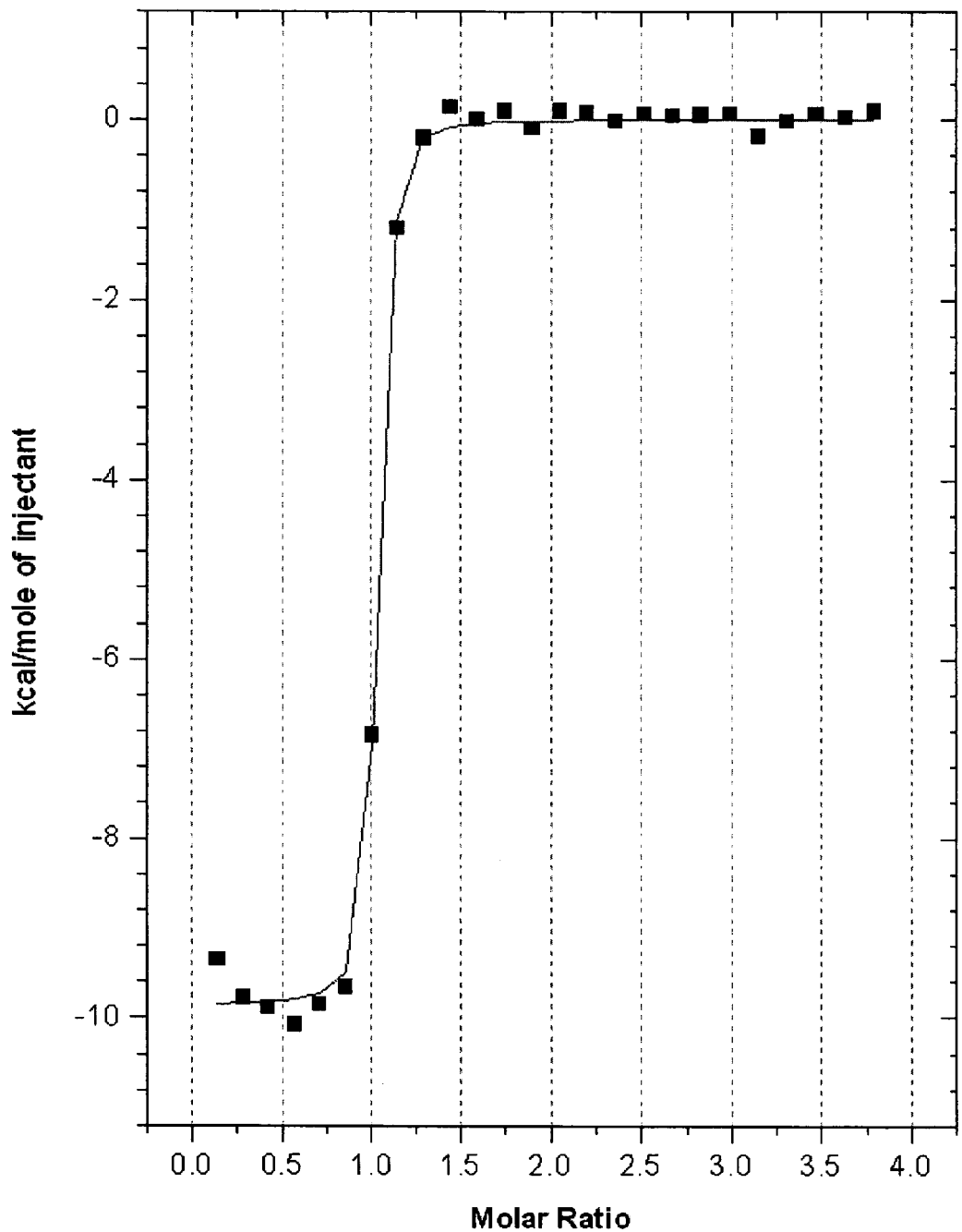
FIG. 2. Determination of the compound of general formula I, namely 4-(5-chloro-2,4-dihydroxyphenyl)-5-(4-ethoxyphenyl)-1,2,3-thiadiazole (3b) binding to Hsp90N by isothermal titration calorimetry. Integrated isothermal titration calorimetric data is shown.
Figure 3:
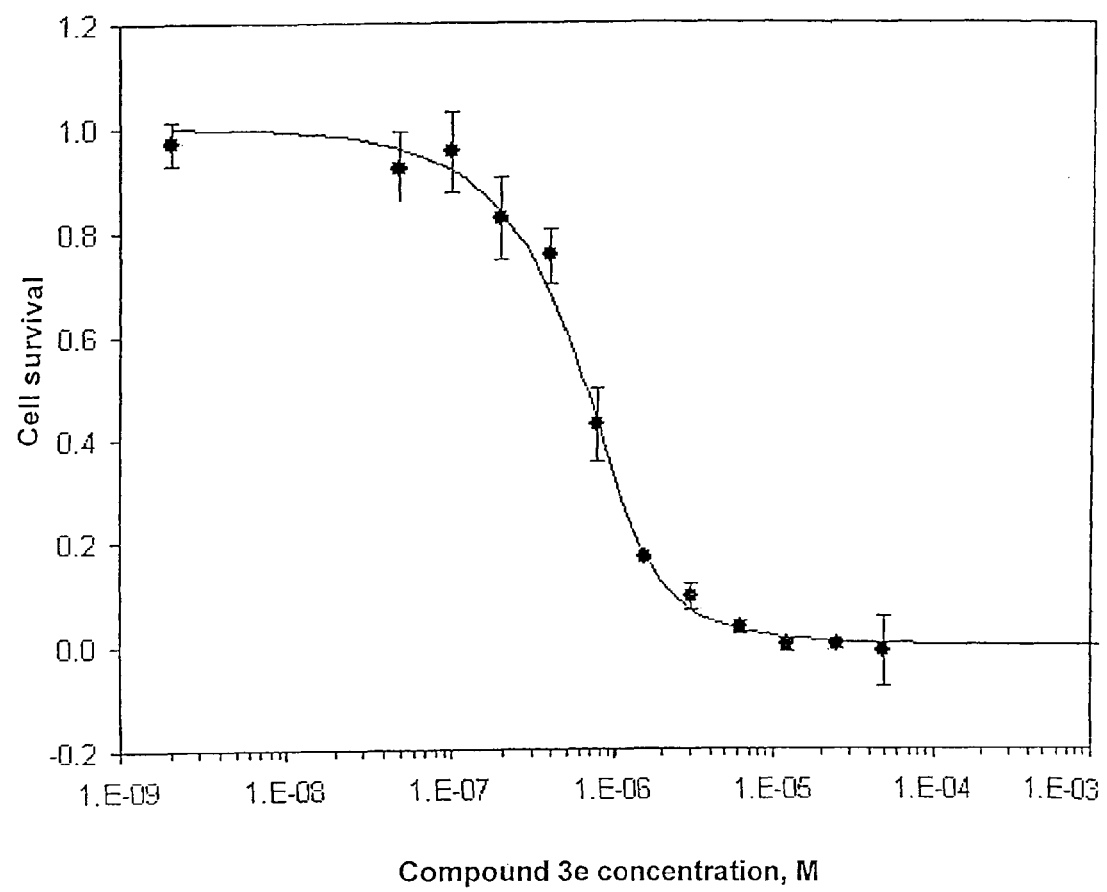
FIG. 3. A typical cell survival curve generated for compound of general formula I, namely 4-(5-ethyl-2,4-dihydroxyphenyl)-5-(4-ethoxyphenyl)-1,2,3-thiadiazole (3e) in U2OS cells. Such curves were used for the determination of compound concentrations where cell growth is reduced by 50% ($GI_{50}$).

Inhibitor binding to the N-terminal domain of Hsp90 were determined by isothermal titration calorimetry (Chaires, J. B. 2008. Annu. Rev. Biophys. 37: 135-51). FIG. 1 shows a representative experimental data—raw isothermal titration calorimetry experiment of compound 3b binding to Hsp90N (50 mM Hepes buffer, 100 mM NaCl, pH 7.5, 37° C.). Protein concentration in the calorimeter cell was 6 μM. Ligand concentration in the syringe was 120 μM. FIG. 2 shows the same data as in FIG. 1 in the integrated form. The binding constant was determined to be $1.3 \times 10^8$ M$^{-1}$ with stoichiometry of 0.97. This is equivalent to dissociation constant equal to 7.5 nM. Such strong binding constants are at the verge of instrument capabilities. Therefore, they may be slightly underestimated. Very steep isothermal titration curves show very tight binding and strong potential as candidate compounds to inhibit Hsp90 activity in vitro.

The values of various compound binding constants to both protein constructs (the N-terminal domain, Hsp90N, and the full length Hsp90F) obtained at 37° C. are listed below. Dissociation constants ($K_d$, determined by isothermal titration calorimetry) of compound binding to the N-terminal domain of Hsp90 (Hsp90N) were: for compound 3a was 0.016±0.004 μM, for compound 3b was 0.035±0.008 μM, for compound 3c was 0.017±0.006 μM, for compound 3d was 0.034±0.003 μM, and for compound 3e with Hsp90N was 0.029±0.002 μM. Similarly, the $K_d$s of the compound binding to the full Hsp90 protein (Hsp90F) were: for compound 3a was 0.039±0.018 μM, for compound 3b was 0.014±0.001 μM, for compound 3c was 0.011±0.007 μM, for compound 3d was 0.057±0.002 μM, and for compound 3e was 0.031±0.005 μM.

Example 12

Determination of Growth Inhibition Constants (GI$_{50}$)

The growth inhibition constants of the compounds were determined in two cancer cell lines: U2OS (osteosarcoma) and HeLa (cervical carcinoma). Cells were maintained in DMEM (HeLa) and a 50-50% mixture of DMEM and F-12 media (U2OS) supplemented with 10% fetal bovine serum. Stock solutions (20 mM) of the tested compounds were prepared in 100% dimethyl-sulfoxide (DMSO). Cells, cultured in 24-well plates, were subjected to a range of concentrations of the compounds (50 mM-0.05 mM) at 0.25% DMSO. After 3 days, cell viability was assayed using XTT (sodium salt of 2,3-bis[2-Methoxy-4-nitro-5-sulfophenyl]-2H-tetrazolium-5-carboxyanilide inner salt) and PMS (phenazine methosulfate) reagents (Scudiero et al. 1988. *Cancer Res.* 48, 4827-4833). Stock solutions of XTT (1 mg/ml) and PMS (1.53 mg/ml) were prepared in Hank's buffered saline (HBS). Culture medium in each well was replaced by 100 μl of Opti-MEM media (Life technologies) containing 35 μg/ml XTT and 0.27 µg/ml PMS. Cells were returned to the incubator for 15-20 min. Quantity of viable cells in each well was evaluated spectrophotometrically measuring the absorbance of XTT formazan at 470 nm. Each experiment was run in duplicate.

The values of various compound growth inhibition constants to U2OS (osteosarcoma) cell line and were the following: for compound 3a was 8.4±1.2 µM, for compound 3b was 15.1±3.4 µM, for compound 3c was 7.1±0.1 µM, for compound 3d was 11.5±0.1 µM, and for compound 3e was 0.65±0.08 µM. Similarly, the $GI_{50}$ constants for HeLa (cervical carcinoma) cell line were: for compound 3a was 2.5±0.1 µM, for compound 3b was 4.2±0.4 µM, for compound 3c was 3.3±0.1 µM, for compound 3d was 3.6±0.3 µM, and for compound 3e was 0.70±0.04 µM. Such strong compound potency in inhibiting cancerous cell growth and survivability indicate compound potential to become lead compounds and candidates for therapeutic anticancer treatment.

The above described new compounds are effective binders of Hsp90 target and they efficiently inhibit cancerous cell growth. The potency of compounds is comparable or better than other patented compounds. Synthesis of new compounds is significantly easier and less expensive than other similar patented compounds with comparable potency.

The invention claimed is:

1. 5-aryl-4-(5-substituted-2,4-dihydroxyphenyl)-1,2,3-thiadiazoles of general formula (I)

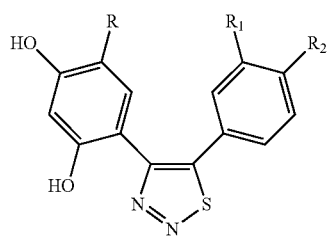

(I)

wherein

R is H, Cl, Br, I, $CH_3$, $OCH_3$, or $C_2H_5$;

$R_1$ and $R_2$ are the same or different substituents, selected from the group consisting of H, $CH_3$, $C_2H_5$, $C_3H_7$, $C_4H_9$, $OCH_3$, $OC_2H_5$, $OC_3H_7$, $O(CH_2)_2O$, $O(CH_2)_3O$ and pharmaceutically acceptable salts thereof.

2. A compound according to claim 1, selected from the group consisting of:

4-(5-chloro-2,4-dihydroxyphenyl)-5-(4-methoxyphenyl)-1,2,3-thiadiazole;

4-(5-chloro-2,4-dihydroxyphenyl)-5-(4-ethoxyphenyl)-1,2,3-thiadiazole;

4-(5-chloro-2,4-dihydroxyphenyl)-5-(4-methylphenyl)-1,2,3-thiadiazole;

4-(5-chloro-2,4-dihydroxyphenyl)-5-(3,4-dimethoxyphenyl)-1,2,3-thiadiazole; and 4-(5-ethyl-2,4-dihydroxyphenyl)-5-(4-ethoxyphenyl)-1,2,3-thiadiazole; and possessing Hsp90 inhibitor properties.

3. 5-chloro-2,4-dihydroxy-phenyl-4-methoxybenzylketone hydrazone—intermediate compound useful for the synthesis of thiadiazoles with general formula (I).

4. 5-chloro-2,4-dihydroxyphenyl-4-ethoxybenzylketone hydrazone—intermediate compound useful for the synthesis of thiadiazoles with general formula (I).

5. 5-chloro-2,4-dihydroxyphenyl-4-methylbenzylketone hydrazone—intermediate compound useful for the synthesis of thiadiazoles with general formula (I).

6. 5-chloro-2,4-dihydroxyphenyl-3,4-dimethoxybenzylketone hydrazone—intermediate compound useful for the synthesis of thiadiazoles with general formula (I).

7. 5-ethyl-2,4-dihydroxyphenyl-4-ethoxybenzylketone hydrazone—intermediate compound useful for the synthesis of thiadiazoles with general formula (I).

8. A composition comprising a thiadiazole according to any one of claims 1 to 2.

* * * * *